(12) United States Patent
Le Couedic et al.

(10) Patent No.: US 7,666,228 B2
(45) Date of Patent: *Feb. 23, 2010

(54) SHOCK-ABSORBING INTERVERTEBRAL IMPLANT

(75) Inventors: Régis Le Couedic, Andresy (FR); Jacques Senegas, Merignac (FR)

(73) Assignee: Zimmer Spine, Bordeaux (FR)

(*) Notice: Subject to any disclaimer, the term of this patent is extended or adjusted under 35 U.S.C. 154(b) by 62 days.

This patent is subject to a terminal disclaimer.

(21) Appl. No.: 11/800,676

(22) Filed: May 7, 2007

(65) Prior Publication Data
US 2007/0213829 A1    Sep. 13, 2007

Related U.S. Application Data

(63) Continuation of application No. 10/332,412, filed as application No. PCT/FR01/02261 on Jul. 12, 2001, now Pat. No. 7,238,204.

(30) Foreign Application Priority Data
Jul. 12, 2000    (FR) .................................. 00 09093

(51) Int. Cl.
*A61F 2/44*    (2006.01)
(52) U.S. Cl. .................................. 623/17.11
(58) Field of Classification Search .... 623/17.11–17.16
See application file for complete search history.

(56) References Cited

U.S. PATENT DOCUMENTS

| 4,511,354 A | 4/1985 | Sterling |
|---|---|---|
| 4,778,474 A | 10/1988 | Homsy |
| 4,871,366 A | 10/1989 | von Recum et al. |
| 5,496,318 A | 3/1996 | Howland et al. |
| 5,645,599 A | 7/1997 | Samani |
| 5,674,294 A | 10/1997 | Bainville et al. |
| 5,836,948 A | 11/1998 | Zucherman et al. |
| 6,258,126 B1 | 7/2001 | Colleran |
| 6,348,054 B1 | 2/2002 | Allen |
| 6,440,169 B1 | 8/2002 | Elberg et al. |
| 6,443,955 B1 | 9/2002 | Ahrend et al. |
| 6,660,038 B2 | 12/2003 | Boyer et al. |
| 6,767,369 B2 | 7/2004 | Boyer et al. |

FOREIGN PATENT DOCUMENTS

| FR | 2 681 525 | 3/1993 |
|---|---|---|
| FR | 2 717 675 | 9/1995 |
| FR | 2 774 581 | 8/1999 |
| WO | WO 94/26195 | 11/1994 |
| WO | WO 99/21501 | 5/1999 |

*Primary Examiner*—Anu Ramana
(74) *Attorney, Agent, or Firm*—Crompton, Seager & Tufte, LLC.

(57)    ABSTRACT

The invention relates to an intervertebral implant comprising a spacer designed to be applied between two spinous processes of two vertebrae. The spacer comprises: two elements (10, 12) made of a first material, and each presenting a first end (10a, 12a) and a second end (10b, 12b), said first end (10a, 12a) being securable to a spinous process; and a connection piece (14) made of a second material of greater elastic deformability than said first material, said connection piece interconnecting said second ends (10b, 12b) of said two elements (10, 12) so that the stresses that are exerted on said two elements (10, 12) are damped, and said connection piece enabling said intervertebral implant to limit and brake the relative movements of said vertebrae.

4 Claims, 3 Drawing Sheets

SHOCK-ABSORBING INTERVERTEBRAL IMPLANT

This Application is a continuation of U.S. application Ser. No. 10/332,412 filed on Jan. 7, 2003, which is a National Stage of PCT/FR01/02261 filed Jul. 12, 2001, which claims priority to French patent 00 09093 filed on Jul. 12, 2000.

FIELD OF THE INVENTION

The present invention relates to an intervertebral implant designed to be applied, in particular, between two spinous processes of two vertebrae.

BACKGROUND OF THE INVENTION

The indications for which this type of implant is inserted and fixed between the spinous processes generally originate from deterioration of the intervertebral disk. In particular, when the posterior portion of an intervertebral disk has deteriorated, extension of the spine causes the two vertebrae that are separated by the disk to move towards each other abnormally. This generally causes the nerve roots to become trapped and causes the person who is affected by this problem to experience pain.

Intervertebral implants comprising a spacer that is inserted between the spinous processes and that includes fixing means are well known. These spacers, generally made of titanium alloy, present a notch at each of their ends, with the spinous processes being received in the notches. In addition, the spacer is held by ties, interconnecting the two opposite edges of each of the notches and tightened around part of the wall of each spinous processes.

Such implants limit the extent to which the vertebrae can move towards each other since, when the spine is in extension, the spinous processes tend to come into abutment against the bottoms of the opposite notches in which they are inserted. However, the material of which the spacer is made is hard compared with the material of an intervertebral disk which, when it is intact, limits the extent to which the vertebrae can move towards each other, so much so that the jolts which can be transmitted to the spine, e.g. while walking, are not damped between two vertebrae interconnected by a spacer. Furthermore, since the spacer does not have the same mechanical properties as the remaining portion of the intervertebral disk, the overall mechanical properties of the spine present significant discontinuities compared with an intact spine, thereby increasing deterioration of the intervertebral disk.

SUMMARY OF THE INVENTION

An object of the present invention is to provide an intervertebral implant having two opposite notches against which the spinous processes come into abutment, which notches present relative mobility with relative movements between them being damped.

To achieve this object the invention provides an intervertebral implant comprising a spacer designed to be applied between two spinous processes of two vertebrae, the implant being characterized in that said spacer comprises:

two elements made of a first material, and each presenting a first end and a second end, said first end being securable to a spinous process; and a connection piece made of a second material of greater elastic deformability than said first material, said connection piece interconnecting said second ends of said two elements so that the stresses that are exerted on said two elements are damped, and said connection piece enabling said intervertebral implant to limit and brake the relative movements of said vertebrae.

Thus, the connection piece situated between the two elements, each secured to a spinous process, tends to become compressed when the spinous processes move towards each other, and absorb the stresses exerted on said two elements. As a result, the vertebrae move towards each other with a certain amount of elasticity that is close to the natural elasticity conferred by an intact intervertebral disk. Furthermore, the relative elastic mobility of the vertebrae is compatible with the elastic deformation of the posterior ligaments which hold the vertebrae together. A system is thus obtained in which, under stress, the relative mobility of its component elements is substantially identical to the relative mobility of the elements of the original intact system, thereby protecting the elements from further deterioration.

In advantageous manner, said second ends of the spacer present a securing wall onto which said connection piece is suitable for being bonded. Thus, no additional fixing member is necessary and the adhesive properties of the second material co-operate with the securing wall.

In a particular embodiment of the invention, said securing wall presents recesses that are suitable for co-operating with projections of said connection piece in such a manner as to increase bonding between said connection piece and said wall. It will be understood that because recesses are formed in a wall, the surface area of said wall is increased, thereby increasing the area of contact between the two materials when one of the materials can be molded onto the wall of the other. The increase in contact area increases the connection forces between said connection piece and said two elements. Furthermore, recesses are formed in such a manner as to increase contact area and also to increase the static friction forces between said two elements and the material of the connection piece, said forces being in addition to the connection forces.

Advantageously, said second material of said connection piece is constituted by a body obtained by polymerization. As a result, the connection piece can easily be hot molded onto said elements if the material is polymerized beforehand, or it can be constituted in situ if the monomers constituting said second material polymerize at a speed that is slow enough to provide enough time to make the assembly.

In a preferred embodiment of the invention, said first material of said elements is a titanium alloy. It is thus easy to form recesses in said securing wall onto which said connection piece is suitable for being bonded.

In a first particular embodiment, each first end of said two elements forms a notch between two wings that is suitable for receiving a spinous process, and said implant further comprises a tie of adjustable length interconnecting said two wings, said tie surrounding a portion of said spinous process in such a manner as to secure said first end to said spinous process.

This characteristic of the intervertebral implant thus resides in the way said elements are fixed onto the spinous processes. A tie is preinstalled on each of said elements of said spacer, and once said spacer is inserted between two processes, said elements are secured to the processes by tightening said ties.

In a second particular embodiment of the invention, each first end of said two elements forms a notch between two wings that is suitable for receiving a spinous process, and said implant further comprises a pin that is suitable for passing laterally through said wings and said process in such a manner as to secure said first end to said spinous process.

In this configuration, the spinous processes are pierced transversely, and the elements are connected thereto by means of a pin or rivet which passes both through the two wings of the element and through the process situated between them. The pin or rivet is fixed onto one or both of the wings in such a manner as to prevent it from being removed accidentally.

In a third particular embodiment of the invention, each first end forms a notch between two wings that is suitable for receiving a spinous process, and said implant further comprises a clip-forming semicircular part interconnecting said wings, said clip surrounding a portion of said spinous process in such a manner as to secure said first end to said spinous process.

As a result, the clips are easily fixed onto the wings of said elements once the spacer has been inserted. As explained in greater detail below, in this particular embodiment, since the wings are disengaged, the spacer is inserted without major surgery on the posterior ligaments.

BRIEF DESCRIPTION OF THE DRAWINGS

Other features and advantages of the invention will appear on reading the following description of particular embodiments of the invention given by way of non-limiting indication with reference to the accompanying drawings, in which.

DETAILED DESCRIPTION OF THE INVENTION

Figure 1:
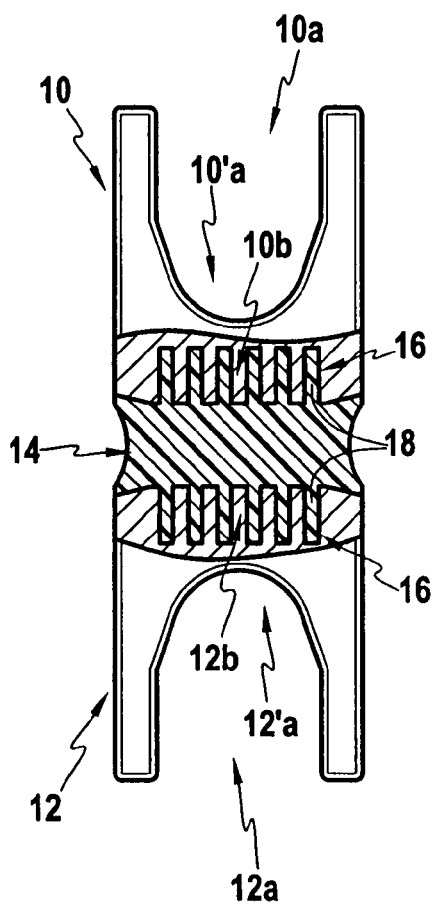
FIG. 1 is an axial section view of an intervertebral spacer of the invention.

The spacer and the method of connecting the elements that constitute it are described initially with reference to FIG. 1.

The intervertebral implant includes two symmetrical elements 10 and 12 each presenting a first end 10a and 12a and a second end 10b and 12b. The two elements 10 and 12 are made of a bio-compatible material of the titanium-alloy type, suitable for remaining permanently inside the body on the spine.

Each first end 10a, 12a presents a notch 10'a, 12'a in which a spinous process is capable of bearing in such a manner that each first end 10a, 12a surrounds substantially half of the circumference of a process, said process passing through the first end 10a, 12a.

The elements 10 and 12 are interconnected by a connection piece 14, interposed between them, in such a manner that said elements 10 and 12 are held symmetrically relative to each other. More precisely, it is the two ends 10b and 12b of the elements 10 and 12 that are interconnected.

The connection piece 14 is constituted by a body, obtained by polymerization, of the plastics-material type. The body is selected from materials having elastic deformability that is greater than that of the material of said elements 10 and 12, and especially having elastic properties that are similar to those of the posterior ligaments which hold the various elements of the spine together.

Organic silicon compounds form polymers having mechanical properties that are capable of being determined by choosing their basic ingredients, in particular by their degree of substitution, the nature of the substituents, and their molecular weight, and having elastic behavior that is preponderant compared with their plastic behavior. Thus, they constitute a family of materials suitable for interconnecting said two elements 10 and 12. Furthermore, these polymers are capable of being highly adhesive on materials of inorganic composition. Thus, when the elements 10 and 12 are made of titanium alloy, the connection piece 14 provides a good connection.

However, suitable polymer-type materials are not restricted to the organic silicon compounds and any other material presenting similar properties could be used.

The material of said connection piece 14 is suitable for bonding onto a securing wall of each of said two substantially plane ends 10b and 12b. However, in order to increase adhesion, recesses 16 are formed in the securing walls of the ends 10b and 12b and these recesses are suitable for co-operating with projections 18 of the connection piece 14 which are inserted in the recesses 16.

This characteristic serves, firstly to increase the contact area between the two materials, thereby increasing the connection force between them in a direction that is normal to said contact surface, and secondly to create static friction forces which are in addition to the bonding force.

Such a connection is made either by injecting the hot polymer between the two elements 10 and 12 held facing each other in a mold, or by molding a cold mixture of monomers between the two elements 10 and 12 if their reaction speed is sufficiently slow. The projections 18 are thus formed in situ when the liquid or semi-liquid polymer inserted in the recesses 18 solidifies after cooling or after chemical reaction. It will be understood that the connection piece 14 is constituted by the polymer interposed between the elements 10 and 12, and that in order to maintain it between the facing elements while it is in the liquid state, the walls of the mold must necessarily surround the space between the two elements 10 and 12 in line with them.

Figure 5:
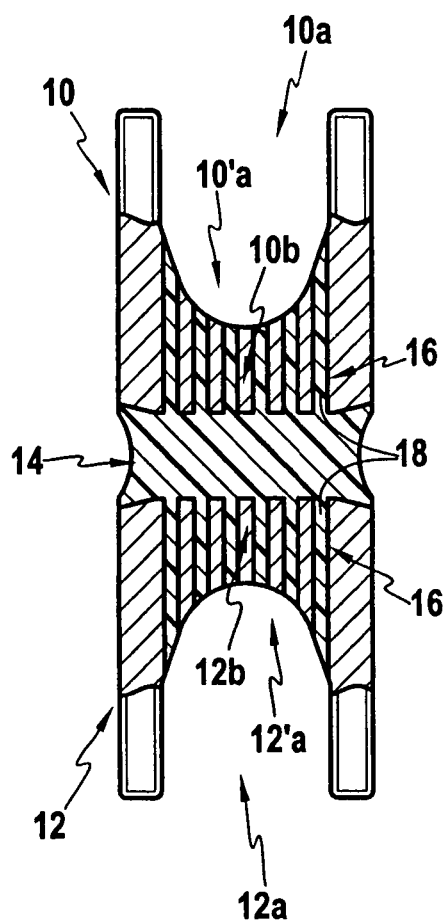
FIGS. 5 and 6 are diagrammatic views showing other embodiments of the intervertebral spacer of the invention.

In a particular embodiment, shown in FIG. 5, the recesses 16 formed in the securing wall open out into the outside wall of the elements 10 and 12 so that the liquid polymer penetrates completely into the recesses 16 without any air being trapped therein. As a result, the connection between the material of the connection piece 14 and the elements is strengthened.

In addition, the recesses, shown parallel to the longitudinal axis of the spacer in FIG. 1, are capable of being formed obliquely relative to the longitudinal axis and/or of being non rectilinear. These configurations enable the static friction forces of the polymer on the elements 10 and 12 to be increased, thereby strengthening their interconnection.

Figure 6:
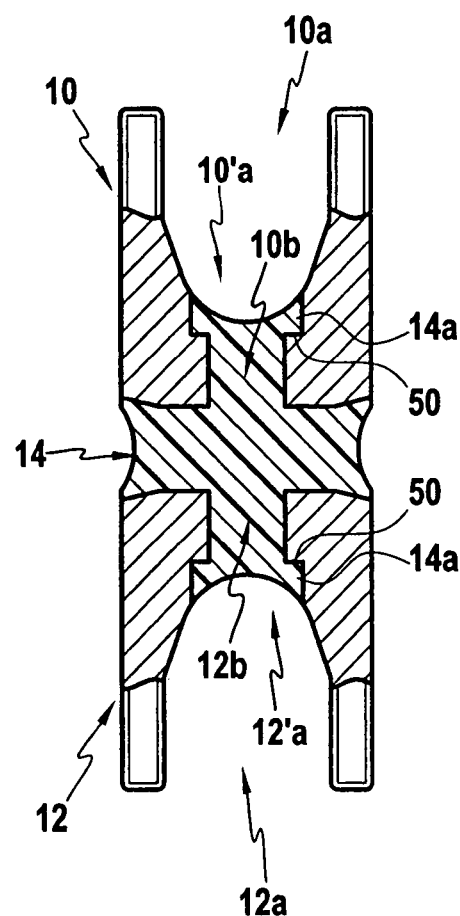

In another embodiment of the invention, shown in FIG. 6, the elements 10 and 12 are axially pierced in the securing walls of their second ends 10b and 12b in order to form a single recess opening out into their first ends 10a and 12a at the bottoms of their notches 10'a and 12'a. A portion 14a of the recess-forming hole situated in the vicinity of the notch presents a diameter that is greater than that of the hole which opens out into the securing wall, in such a manner as to form a shoulder 50. The connection piece is thus molded between the elements 10 and 12 in such a manner that the polymer-type material penetrates into the two recesses and fills them completely as far as the bottom surfaces of their notches 10'a and 12'a. Furthermore, the diameter of the holes is greater than the diameter of the recesses shown in FIG. 1. Thus, once the material of the polymer type has set, it not only secures the two elements 10 and 12 by means of its adhesive properties on the inside walls of the holes, but it also secures them mechanically since the portions of material molded in said greater-diameter portions come into abutment against said shoulders.

Particular embodiments of the invention are described below with reference to FIGS. 2, 3, and 4.

Figure 2:
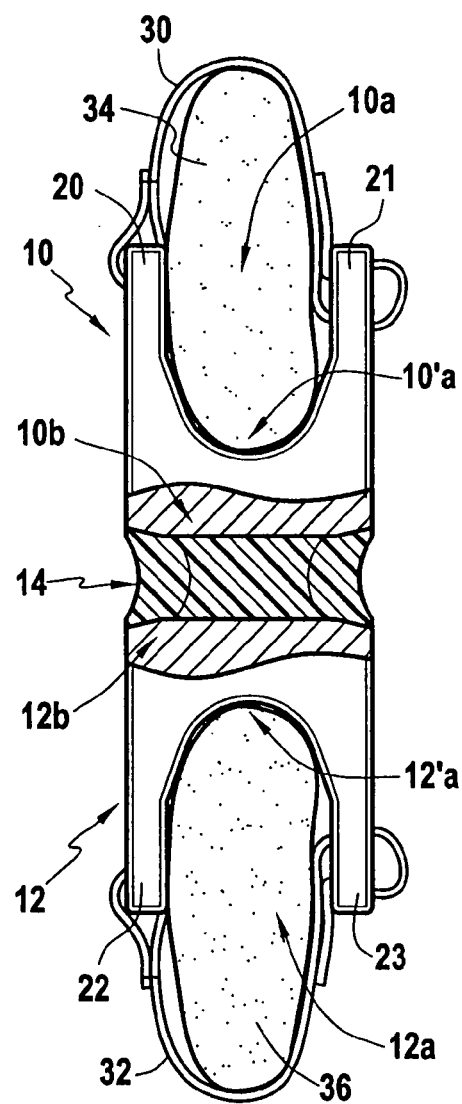
FIG. 2 is a diagrammatic view in elevation showing the intervertebral implant provided with its adjustable fixing ties.

FIG. 2 shows a first particular embodiment of the invention in which the two opposite edges of the notches 10'a and 12'a form wings 20, 21, 22, 23 interconnected in pairs by ties 30 and 32 each having a portion between said wings 20, 21, and 22, 23 of a length that is adjustable, and each being locked by the tension which can be applied on said ties 30 and 32.

FIG. 2 shows the two elements 10 and 12 connected by the connection piece 14. The implant of the invention is inserted between two spinous processes 34, 36 of two adjacent vertebrae in such a manner that the two notches 10'a and 12'a, facing in opposite directions, respectively engage part of the adjacent bottom portion of the upper spinous processes 34 and part of the adjacent top portion of the lower spinous processes 36.

The ties 30 and 32 respectively pass round the top portion of the upper spinous process 34 and the bottom portion of the lower spinous process 36 in such a manner that the spinous processes 34 and 36 are capable of being locked in the respective notches 10'a and 12'a. Locking is performed by tightening the ties 30 and 32, which, by means of slots made in the wings 21 and 23, are trapped in said wings 21 and 23.

Thus, the elements 10 and 12 are secured to the respective processes 34 and 36, and relative movement of said processes 34, 36 is possible within the deformation limits of the connection piece 14 made of polymer-type material.

When the two spinous processes 34 and 36 move towards each other, in particular during extension of the spine, the two elements 10 and 12 compress the connection piece 14 in elastic manner, i.e. the reaction force which tends to hold the spinous processes 34 and 36 apart from each other is substantially proportional to the relative displacement of the two processes. Thus, the implant can take over the role of the intervertebral disk to be replaced (or the portion of the intervertebral disk to be replaced) concerning the spacing that it serves to maintain between two vertebrae so as not to trap any roots. It also makes it possible for resulting stresses which are applied to the spinous processes to be compatible with the stresses exerted on the processes by the posterior ligaments.

Furthermore, when the two spinous processes 34 and 36 move away from each other, when bending the spine, the connection piece is subjected to traction having a return force that is also substantially proportional to the elongation to which it has been subjected, at least for small amplitudes. The spine can thus bend through greater amplitude than that which is possible when the two spinous processes are secured to each other in fixed manner.

Figure 3:
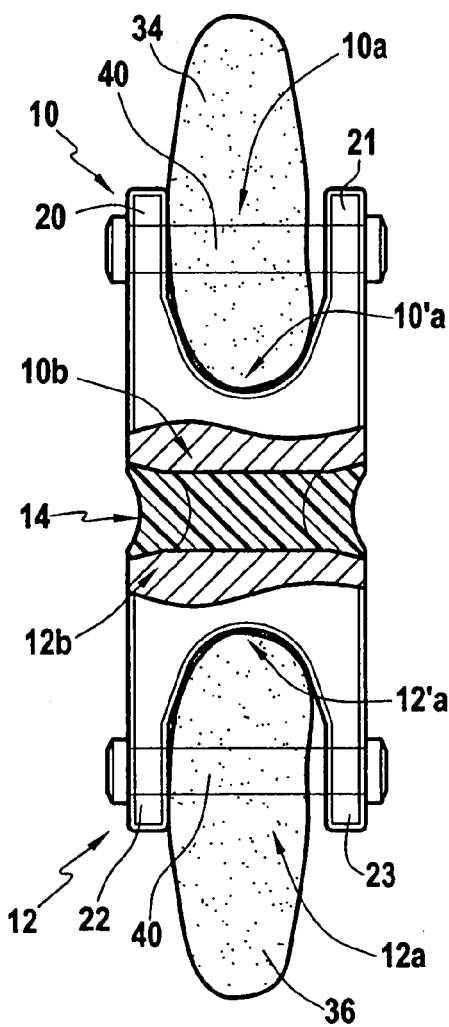
FIG. 3 is a diagrammatic view in elevation showing the intervertebral implant provided with fixing pins.

FIG. 3 shows a second particular embodiment of the invention in which the wings of the notches, and the spinous processes which are inserted between them, are locked together by a pin which passes through the spinous processes.

FIG. 3 shows the intervertebral spacer between the two spinous processes 34 and 36, and the pairs of wings 20, 21 and 22, 23 which engage parts of the processes 34 and 36. Furthermore, respective pins 40 pass through the notches 10'a and 12'a as well as through the spinous process 34 and 36. The wings 20, 21 and 22, 23 are respectively pierced with two facing orifices through which the pins 40 can be inserted and fixed via their ends.

Prior to inserting the implant between the spinous processes 34, 36, said spinous processes are pierced laterally with respective orifices having a diameter that is greater than the diameter of the pins 40. The intervertebral spacer is then inserted between the spinous processes 34, 36, and the rivet-forming pins 40 are then slid through the wings 20, 21 and 22, 23 and the corresponding spinous processes 34, 36. The ends of the pins 40 are flattened longitudinally in such a manner as to give them a diameter that is greater than that of the orifices in the wings 20, 21 and 22, 23 through which they pass. In this way, the pins 40 are locked in longitudinal translation relative to the spacer, and the two elements 10 and 12 are thus respectively secured to the spinous processes 34 and 36.

In this second particular embodiment of the invention, it is not necessary to remove the interspinous ligaments or to disinsert the supraspinous ligaments that underlie and overlie the intervertebral space in which the spacer is to be inserted.

During insertion of the spacer, since the pairs of wings 20, 21 and 22, 23 are not interconnected by means suitable for surrounding the spinous process, it is necessary to remove the interspinous ligaments and to disinsert the supraspinous ligaments only from the intervertebral space in which the spacer is to be inserted.

Figure 4:
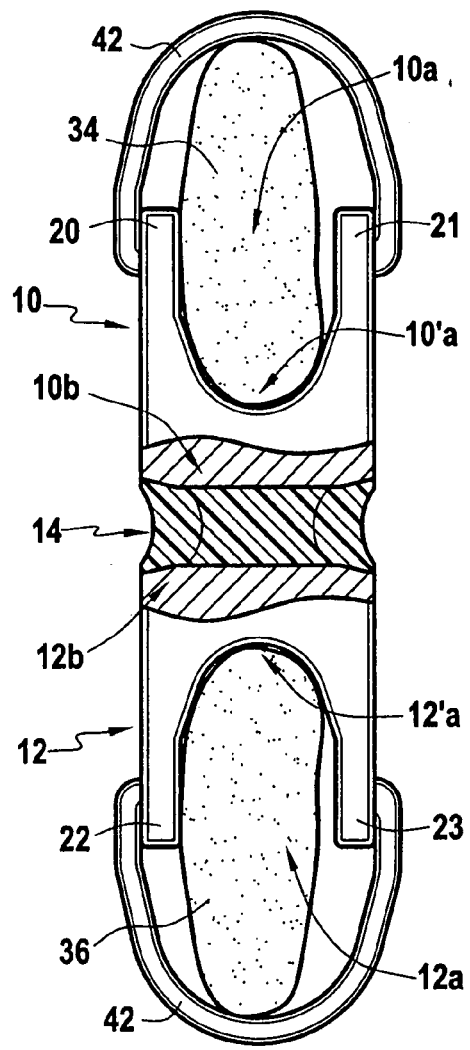
FIG. 4 is a diagrammatic view in elevation showing the intervertebral implant provided with fixing clips.

FIG. 4 shows a third embodiment of the invention providing the same advantages as those described above for the second embodiment.

FIG. 4 shows the intervertebral spacer between the two spinous processes 34 and 36, and the pairs of wings 20, 21 and 22, 23 which engage parts of the processes 34 and 36. In contrast, the elements 10 and 12 of the intervertebral spacer are secured to the spinous processes 34 and 36 by means of respective clip-forming semicircular parts 42.

The semicircular part 42 includes two hook-forming ends that are directed towards the inside of the part, and that are suitable for being inserted into the orifices formed in the outside walls of the pairs of wings 20, 21 and 22, 23. The part 42 is elastically deformable so that it is force-fitted onto the elements 10 and 12.

Once the spacer has been inserted between the spinous processes 34, 36, the clips 40 are fixed on the elements 10 and 12 in such as manner that the inside walls of the semicircular parts 42 cover wall portions of the spinous processes that complement the wall portions of the spinous processes covered by the notches 10'a and 12'a. The spinous processes 34 and 36 are thus held in the notches 10'a and 12'a by the clips 42, thereby securing the elements 10 and 12 to said spinous processes.

The above-described embodiments of the invention are not limited solely to an intervertebral implant that is suitable for being interposed between two adjacent vertebrae. Thus, it is not beyond the ambit of the invention to provide an implant that is constituted by two implants as described above, which are interconnected via the ends of their wings, along their longitudinal axis, in such a manner as to limit and brake the relative movements of three consecutive vertebrae.

The invention claimed is:

1. An intervertebral implant comprising a spacer designed to be applied between two spinous processes of two vertebrae, said spacer comprising:

two elements made of a first material, each element having a first end and a second end, the first end of each element having an outside wall and including two wings configured to form there between a notch to receive a spinous process, the second end of each element having a securing wall provided with at least one recess, the recess opening out into the outside wall of the first end of the respective element; and a connection piece made of a second material, the second material having sufficient elastic deformability to enable movement of the two elements relative to each other and the second material being configured to bond to said first material, said connection piece being in direct contact with said securing walls of said two elements, said connection piece presenting projections inserted in said recesses so as to increase bonding between said connection piece and said two elements, whereby said connection piece enables said intervertebral implant to limit and brake relative movements of said vertebrae.

2. The intervertebral implant according to claim 1, wherein the implant further comprises a pin for passing laterally through said wings and said process to secure said first end to said spinous process.

3. The intervertebral implant according to claim 1, wherein said implant further comprises a clip forming a semicircular part interconnecting said wings, said clip for surrounding a portion of said spinous process to secure said first end to said spinous process.

4. The intervertebral implant according to claim 1, wherein the implant further comprises a tie for adjustable length interconnecting the two wings, the tie configured to surround a portion of the spinous process to secure the first end to the spinous process.

* * * * *